(12) United States Patent
Shields et al.

(10) Patent No.: US 8,937,561 B2
(45) Date of Patent: *Jan. 20, 2015

(54) SYSTEM AND METHOD FOR CONTROL OF MEDICAL EQUIPMENT USING MULTIPLE WIRELESS DEVICES

(75) Inventors: Gregory Shields, Saratoga Springs, UT (US); Robert H. Woodward, Lindon, UT (US)

(73) Assignee: Canyon Ridge Resources, L.L.C., Lindon, UT (US)

(*) Notice: Subject to any disclaimer, the term of this patent is extended or adjusted under 35 U.S.C. 154(b) by 309 days.

This patent is subject to a terminal disclaimer.

(21) Appl. No.: 13/448,177

(22) Filed: Apr. 16, 2012

(65) Prior Publication Data

US 2013/0099902 A1    Apr. 25, 2013

Related U.S. Application Data

(63) Continuation-in-part of application No. 12/272,592, filed on Nov. 17, 2008, now Pat. No. 8,159,370.

(51) Int. Cl.
*H03M 11/00* (2006.01)
*G05B 11/01* (2006.01)
(Continued)

(52) U.S. Cl.
CPC .............. *G05B 11/01* (2013.01); *A61B 5/7475* (2013.01); *G05G 1/02* (2013.01); *G05G 1/30* (2013.01);
(Continued)

(58) Field of Classification Search
CPC ...... H01H 9/24; H01H 9/26; H01H 2225/018
USPC ............... 341/20, 22; 378/114, 189; 600/437, 600/126; 200/5 C
See application file for complete search history.

(56) References Cited

U.S. PATENT DOCUMENTS 5,179,829 A    1/1993    Grecksch et al.
5,206,894 A    4/1993    Makrinos et al.
(Continued)

FOREIGN PATENT DOCUMENTS

EP    1498082 A1    1/2005
EP    1 649 812      4/2006
(Continued)

OTHER PUBLICATIONS

U.S. Appl. No. 12/272,657, filed Nov. 17, 2008; Shields; notice of allowance issued May 25, 2012.
(Continued)

*Primary Examiner* — Albert Wong
(74) *Attorney, Agent, or Firm* — Thorpe North & Western LLP

(57) ABSTRACT

A system and method for controlling a body-scanning device using multiple wireless devices is disclosed. The method includes communicating a secure wireless signal from a footswitch enclosure to a footswitch receiver coupled to the body scanning device in response to an actuation of a footswitch zone carried on a footswitch enclosure. Additionally, a wireless signal is communicated from a handswitch enclosure in response to an actuation of a handswitch zone and communicated to a handswitch receiver located in the footswitch enclosure. The wireless signal is then communicated from the footswitch enclosure to the footswitch receiver coupled to the body-scanning device to enable an operator to control the body-scanning device using the handswitch or the footswitch.

20 Claims, 14 Drawing Sheets

(51) Int. Cl.

| | | |
|---|---|---|
| *A61B 5/00* | (2006.01) | |
| *G05G 1/02* | (2006.01) | |
| *G05G 1/30* | (2008.04) | |
| *G01R 33/36* | (2006.01) | |
| *A61B 6/00* | (2006.01) | |
| *A61B 8/00* | (2006.01) | |
| *A61B 5/055* | (2006.01) | |
| *G06F 19/00* | (2011.01) | |
| *H01H 3/14* | (2006.01) | |
| *H01H 9/02* | (2006.01) | |

(52) U.S. Cl.
CPC ............ *G01R 33/3692* (2013.01); *A61B 6/467* (2013.01); *A61B 8/467* (2013.01); *A61B 5/055* (2013.01); *G06F 19/3412* (2013.01); *H01H 3/14* (2013.01); *H01H 9/0235* (2013.01); *A61B 6/548* (2013.01); *A61B 8/4472* (2013.01)
USPC ............. 341/20; 378/114; 378/189; 600/437; 600/126

(56) References Cited

U.S. PATENT DOCUMENTS

| | | | |
|---|---|---|---|
| 5,247,449 | A | 9/1993 | Yoshida |
| 5,656,799 | A | 8/1997 | Ramsden et al. |
| 6,074,388 | A | 6/2000 | Tockweiler et al. |
| 6,128,528 | A | 10/2000 | Ericksen et al. |
| 6,368,269 | B1 | 4/2002 | Lane |
| 6,437,963 | B1 | 8/2002 | Hamilton et al. |
| 6,958,701 | B1 | 10/2005 | Storkamp et al. |
| 7,283,615 | B2 | 10/2007 | Morehead |
| 7,298,824 | B2 | 11/2007 | Watanabe |
| 2001/0055368 | A1 | 12/2001 | Carroll |
| 2002/0067407 | A1 | 6/2002 | Cooper |
| 2002/0150214 | A1 | 10/2002 | Spahn |
| 2003/0068006 | A1 | 4/2003 | Beyerlein et al. |
| 2004/0115591 | A1 | 6/2004 | Warner |
| 2004/0230214 | A1 | 11/2004 | Donofrio et al. |
| 2005/0080403 | A1 | 4/2005 | Takahashi |
| 2005/0147940 | A1 | 7/2005 | Mace |
| 2005/0211908 | A1 | 9/2005 | Dieras et al. |
| 2005/0251228 | A1 | 11/2005 | Hamel |
| 2006/0023839 | A1 | 2/2006 | Shoji |
| 2006/0109080 | A1 | 5/2006 | Tang et al. |
| 2006/0188071 | A1 | 8/2006 | Spahn |
| 2006/0203250 | A1 | 9/2006 | Regn et al. |
| 2006/0215817 | A1 | 9/2006 | Watanabe |
| 2006/0278509 | A1 | 12/2006 | Marcus et al. |
| 2007/0043339 | A1 | 2/2007 | Horvath et al. |
| 2007/0093713 | A1 | 4/2007 | Byron |
| 2007/0098237 | A1 | 5/2007 | Yoo et al. |
| 2007/0183574 | A1 | 8/2007 | Morehead |
| 2007/0197163 | A1 | 8/2007 | Robertson |
| 2007/0254261 | A1 | 11/2007 | Rosenblood et al. |
| 2007/0257197 | A1 | 11/2007 | Gordon, III et al. |
| 2008/0194950 | A1 | 8/2008 | Mejia |
| 2009/0167487 | A1 | 7/2009 | Shah et al. |

FOREIGN PATENT DOCUMENTS

| | | |
|---|---|---|
| FR | 2884132 | 10/2006 |
| JP | 2005007086 | 1/2005 |
| JP | 2007117632 | 5/2007 |
| WO | WO 2005/043569 A1 | 5/2005 |
| WO | WO 2005/053561 | 6/2005 |
| WO | WO 2007/084668 | 7/2007 |

OTHER PUBLICATIONS

EP Application EP09826969.9; filing date Nov. 17, 2009; Canyon Ridge Resources; European Search Report dated Oct. 20, 2014.

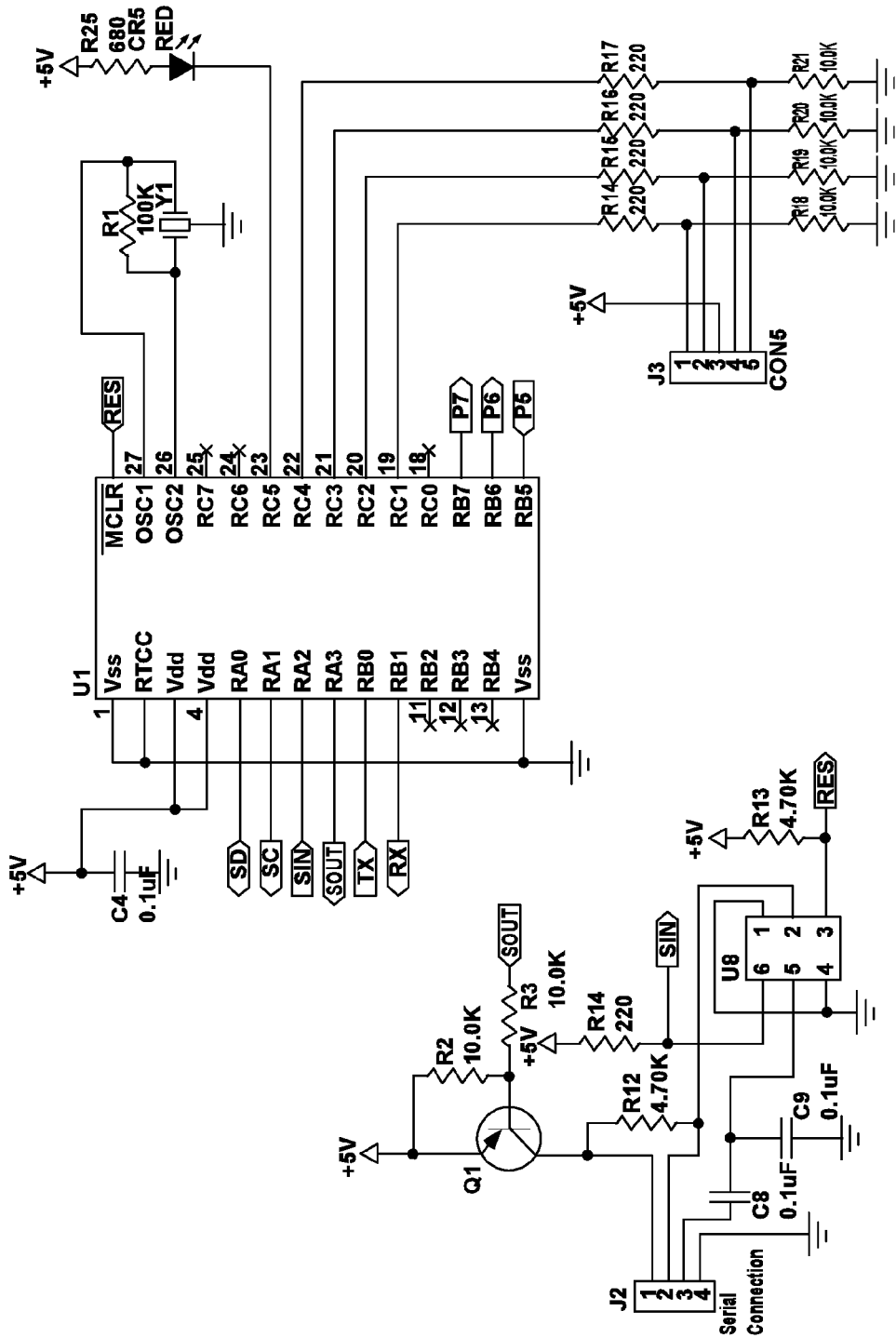
FIG. 6a(1)

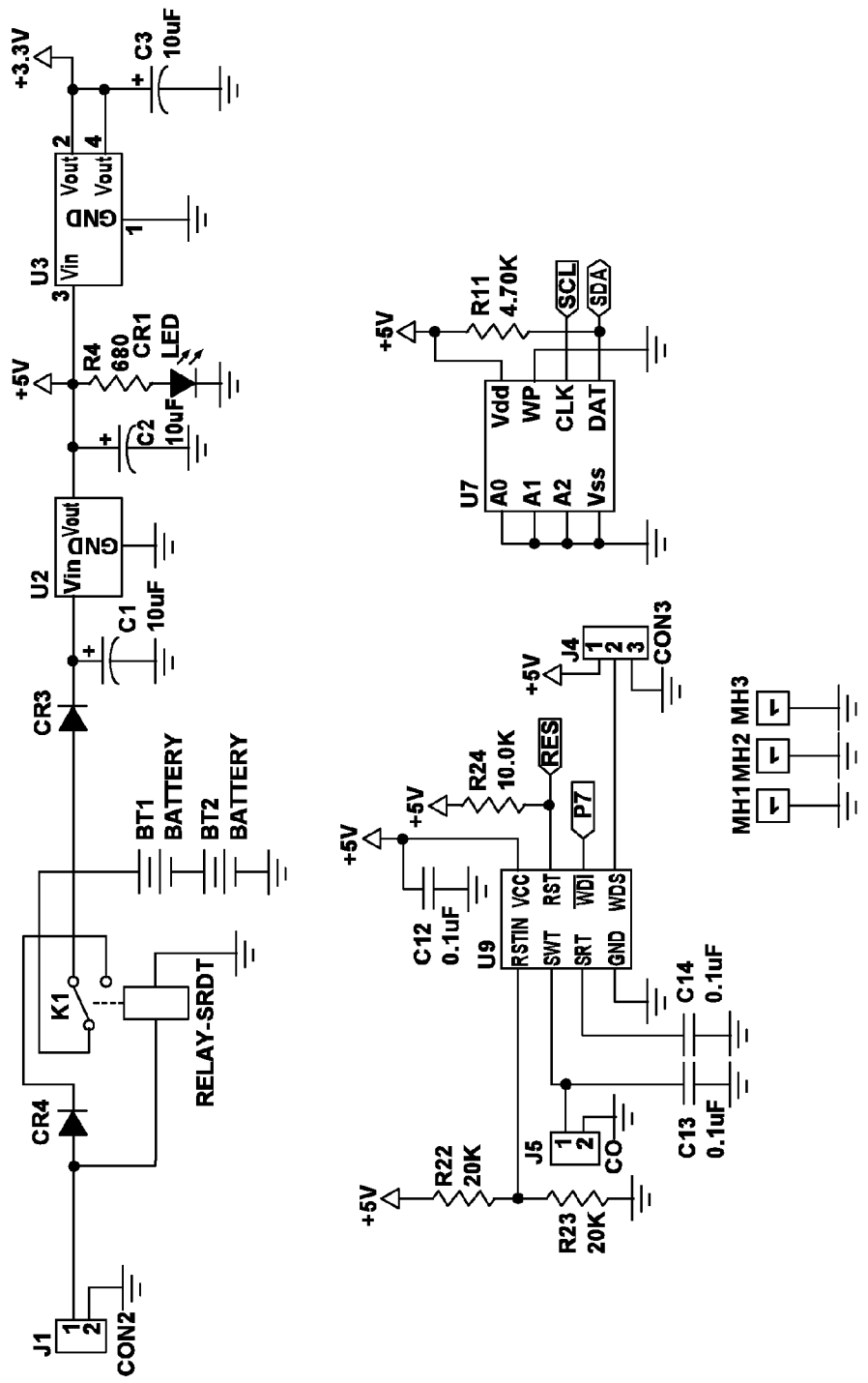
FIG. 6a(2)

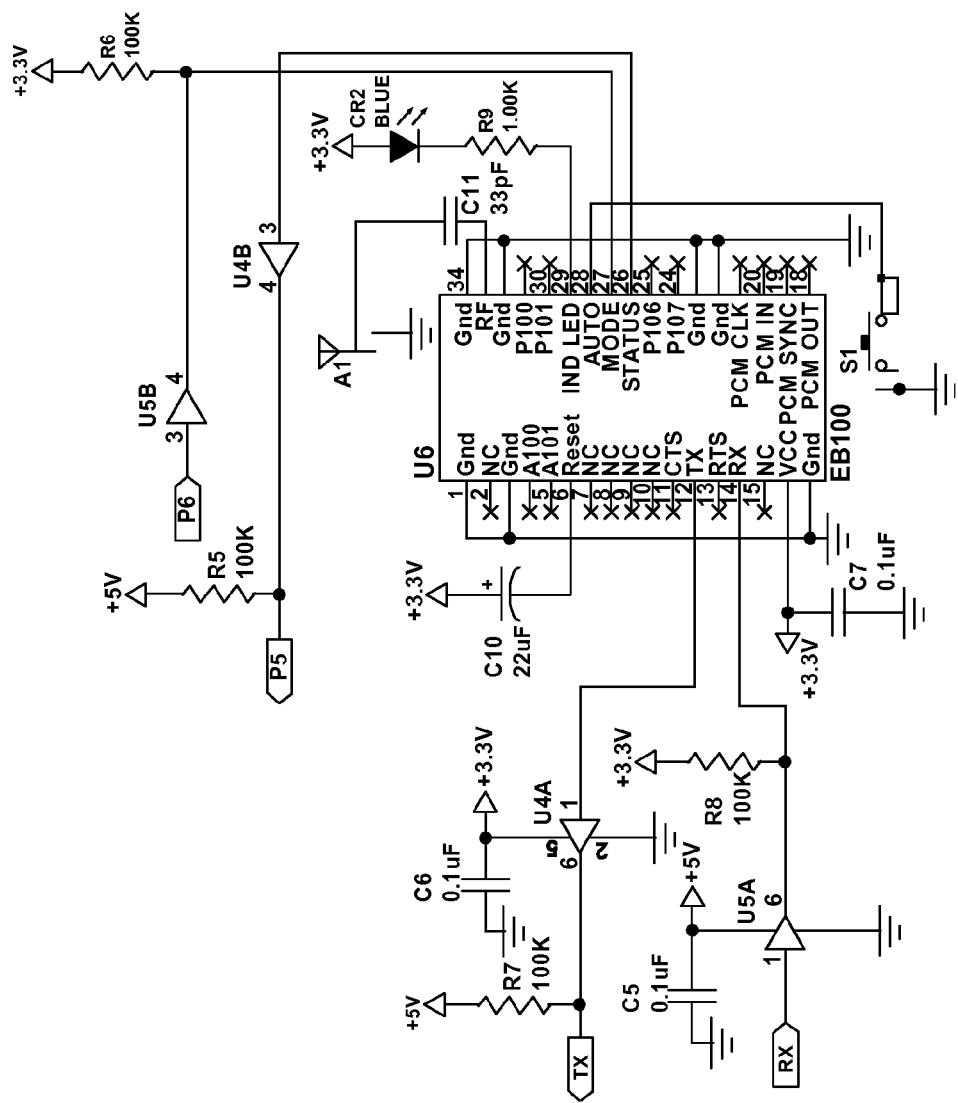
FIG. 6a(3)

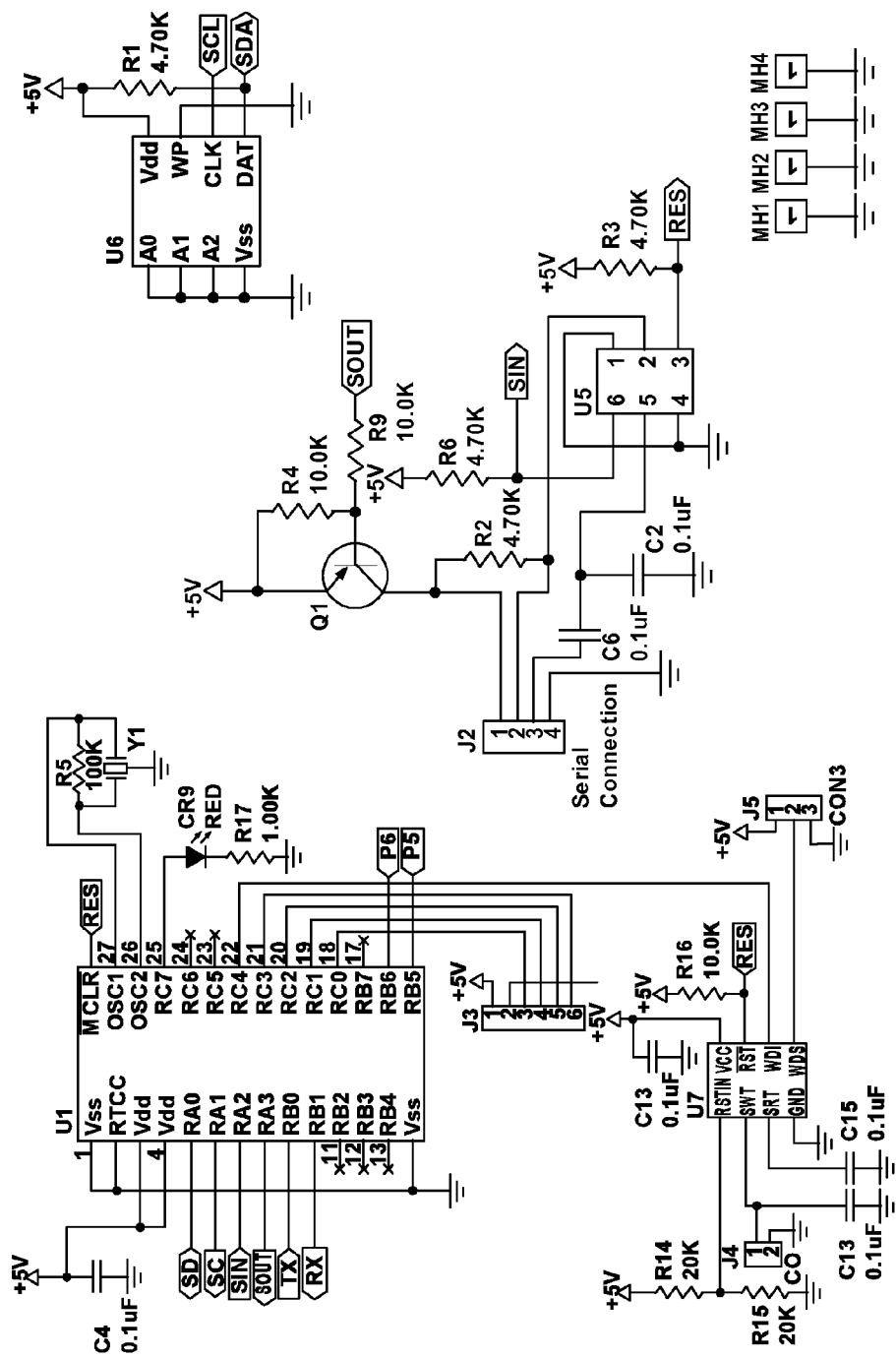
FIG. 6b(1)

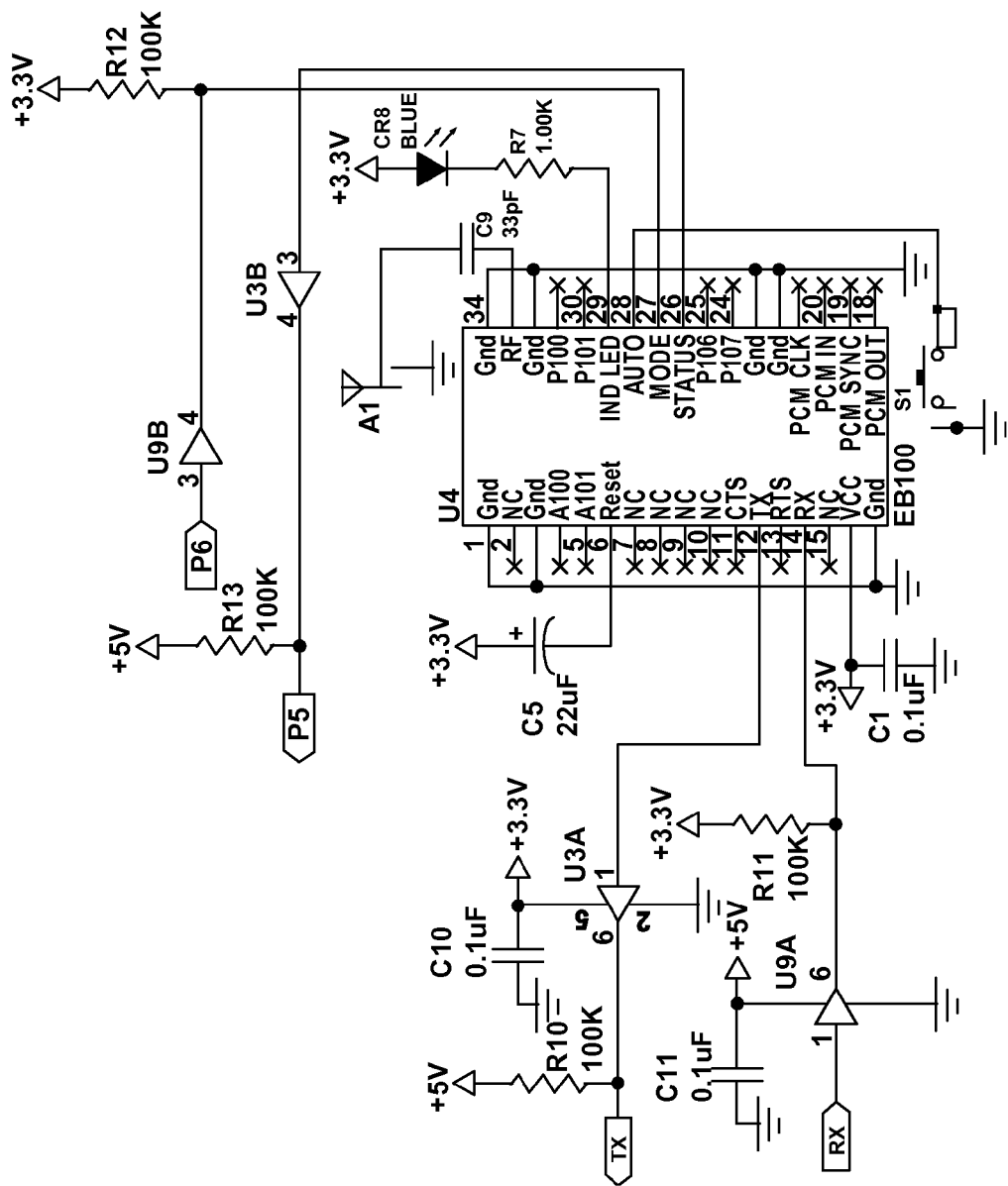
FIG. 6b(2)

SYSTEM AND METHOD FOR CONTROL OF MEDICAL EQUIPMENT USING MULTIPLE WIRELESS DEVICES

RELATED APPLICATIONS

This is a continuation-in-part of U.S. patent application Ser. No. 12/272,592 filed on Nov. 17, 2008.

BACKGROUND

Complex medical devices are typically created by large companies that have the research and development capabilities to develop the devices. For example, scanning and imaging devices such as fluoroscopes, magnetic resonance imagers, nuclear magnetic resonance imagers, ultrasound imagers, and even proton scanners have been developed. These devices can cost millions of dollars each. Once a hospital or health care facility owns such a device, they usually use the device for years, even decades to recover their investment in the device.

However, once the devices have been developed and sold, there is often little incentive for these large companies to make improvements to their devices. After several years, displays, communication systems, software, and graphical interfaces can become outdated, thereby making the expensive medical devices less attractive to use by employees and diminishing the potential profitability of the devices to hospitals and clinics.

For example, the operation of body-scanning devices can require a large number of operations and controls to properly setup the scanning device for a selected patient and provide the desired images. Most scanning devices have cumbersome, relatively non-ergonomic input devices. Use of these input devices can cause users to become tired. Over an extended period of time, the use of standard input devices supplied with body-scanning devices can even cause repetitive motion problems.

BRIEF DESCRIPTION OF THE DRAWINGS

Features and advantages of the invention will be apparent from the detailed description which follows, taken in conjunction with the accompanying drawings, which together illustrate, by way of example, features of the invention; and, wherein:

FIG. 2b is a side view illustration of the footswitch of FIG. 2a;

FIG. 2c is a bottom view of the footswitch of FIG. 2a;

FIGS. 6a(1)-6a(3) is an illustration of an electrical schematic for a handswitch transmitter operable to communicate with the footswitch in accordance with an embodiment of the present invention FIGS. 6b(1)-6b(2) is an illustration of an electrical schematic for a handswitch receiver hardwired to the wireless footswitch transmitter in accordance with an embodiment of the present invention;

Reference will now be made to the exemplary embodiments illustrated, and specific language will be used herein to describe the same. It will nevertheless be understood that no limitation of the scope of the invention is thereby intended.

DETAILED DESCRIPTION OF EXAMPLE EMBODIMENTS

Figure 1:
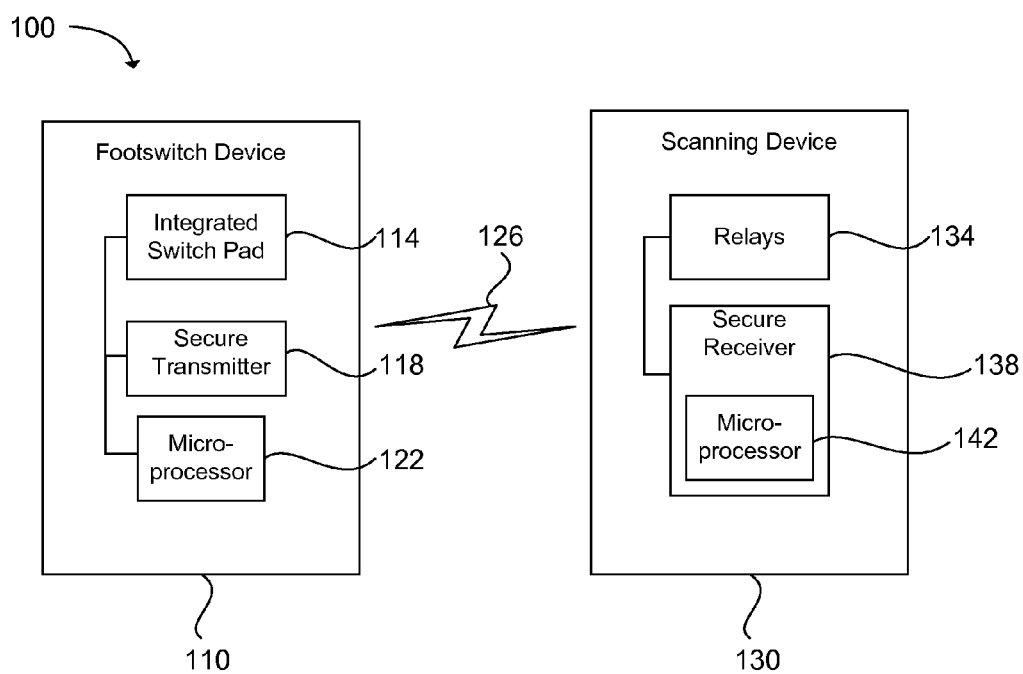
FIG. 1 is an illustration of a wireless footswitch system in accordance with an embodiment of the present invention.

An ergonomic wireless footswitch system for controlling a body-scanning device is disclosed. The wireless footswitch system 100, as illustrated in FIG. 1, includes a footswitch device 110. In one embodiment, the footswitch device can include an integrated switch pad 114. The integrated switch pad can include a plurality of substantially flat switch zones that are actuatable with a user's foot. For example, a user can actuate one of the plurality of switch zones by placing their foot over the switch zone and applying pressure. While examples are provided of the substantially flat switch zones, this is not intended to be limiting. Each switch zone, referred to as a footswitch zone, may or may not be substantially flat. The actuation of the footswitch zone can be detected by a microprocessor 122. The microprocessor can send predetermined data to a secure transmitter 118 communicating which of the plurality of switch zones are activated.

The footswitch system 100 can be used to control body-scanning devices such as an x-ray emitting device, a fluoroscope, a magnetic resonance imager, a nuclear magnetic imager, an ultrasound imager, and a proton scanner. The footswitch system can also be used to control portable devices such as a portable X-ray unit, a portable C-arm type X-ray unit, or a fixed type x-ray room used for radiography, fluoroscopic imaging, and other types of imaging. The term body-scanning device is intended to include both body imaging devices and body scanning devices. The term is also intended to include devices that only image or scan a portion of a body such as an appendage.

Due to the nature of the setting in which body-scanning devices are located, and the nature of the body-scanning device itself, the use of a secure connection between the transmitter and receiver can provide substantial benefits. For example, the body-scanning device may be located in a large hospital having hundreds of types of medical equipment, electronic devices, computers, and so forth. Each of these pieces of medical equipment can radiate intended or unintended electromagnetic signals, thereby creating a relatively noisy electrical environment. The medical equipment, computers, and electronic devices may be used in life sustaining operations. Therefore, unintended communication with these devices can be potentially catastrophic. Additionally, certain types of devices, such as body-scanning devices, can emit potentially harmful rays such as x-rays, proton beams, and the like. Thus, the reception of any wireless commands at these devices should be verifiable with a substantially high degree of confidence that an action, such as the potentially dangerous emission of radiation, is intended. While examples are provided of a secure communication system, this is not intended to be limiting. The transmitters and receivers in the communication system can also be configured to communicate via a non-secure communication link.

To enable wireless transmission from the footswitch system 100 that can be used to control a body-scanning device 130, several steps can be taken. The data from the microprocessor may be scrambled using encryption algorithms, error correction encoding and so forth. The secure transmitter 118 can wirelessly transmit 126 symbols corresponding to the scrambled data from the microprocessor 122. The scrambling of the data can ensure that only a desired device can receive and interpret the data, thereby substantially reducing unintended operation of extraneous medical devices. Additionally, the symbols that are transmitted can also be spread using a pseudorandom noise (PN) code. Spreading of the symbols can minimize the probability that the data can be detected and received by a non-intended receiver that does not have knowledge of the specific PN code. The data may also be transmitted using multiplexing such as time or space division multiplexing.

The symbols transmitted from the secure transmitter 118 can be received by a secure receiver 138. The secure receiver can detect, receive, despread, decrypt, and demultiplex the symbols as necessary to convert the symbols to data. The secure receiver may include error correction decoders to minimize transmission and reception errors in the symbols communicated between the secure transmitter and secure receiver.

To further enhance security, the secure transmitter 118 and secure receiver 138 can be configured to be paired. In one embodiment, the transmitter/receiver pair can establish a trusted relationship by sharing a passkey. The paired passkey can be installed in the transmitter and receiver at a period prior to a user's purchase of the transmitter and receiver. For example, the receiver can cryptographically authenticate the identity of the transmitter by decrypting a transmitted passkey. Once the passkey has been verified as the correct key, a channel having a designated address can be permanently assigned between the transmitter and receiver.

Data that has been received and recovered at the secure receiver 138 can be communicated to a microprocessor 142. The microprocessor can be used to translate the data into a desired format for use by the body-scanning device 130. In one embodiment, the secure receiver and microprocessor can be connected to the body-scanning device through a standard connection, such as a connection that was previously designated for use with a wired control. For example, the secure receiver and microprocessor can be coupled to or contained within a housing that can be connected to a standard input that is used to control the body-scanning device. The data output from the secure receiver to the body-scanning device can be used to relay 134 actuations that activate or deactivate a desired function within the scanning device. The data output from the microprocessor may be formatted in a form that is acceptable to the scanning device.

Figure 2A:
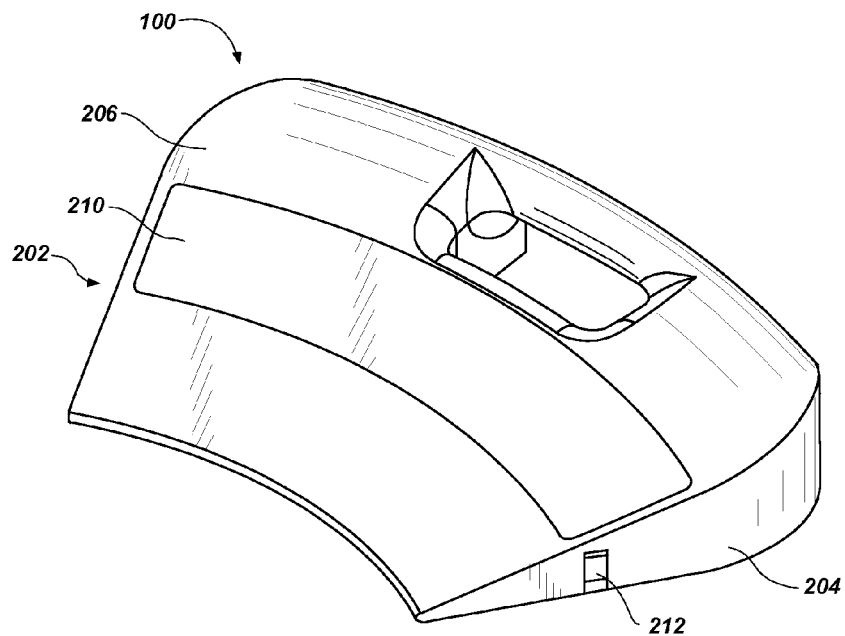
FIG. 2a is a perspective view illustration of an ergonomic wireless footswitch in accordance with an embodiment of the present invention.
Figure 2B:
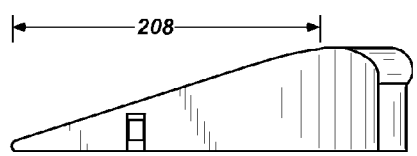
Figure 2C:
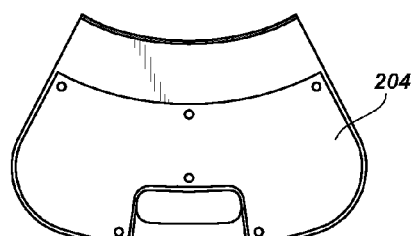

One embodiment of the footswitch system 100 is illustrated in FIGS. 2a-2c. The footswitch system can include a footswitch enclosure 202 having a first side 204 and a second side 206. The first side can be a bottom side of the enclosure and the second side can be a top side of the enclosure. The bottom side can be substantially level with a surface on which the enclosure is placed. The enclosure can have a substantially linear gradient over at least a section of the distance between the first side and the second side. For example, over the distance 208, there is a linear gradient as the top side increases in distance from the bottom side. This shape provides a natural contour on which a user can rest his or her foot on the enclosure with minimal strain or fatigue. The enclosure can include at least one recharging port 212 operable to enable a power source to be connected to allow a battery power storage source within the enclosure to be recharged.

Figure 2D:
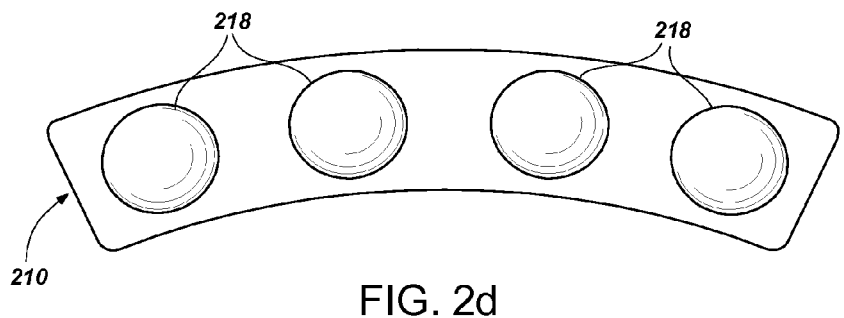
FIG. 2d is an illustration of an integrated switch pad containing a plurality of substantially flat switch zones in accordance with an embodiment of the present invention.

An integrated switch pad 210 can be carried on the top side 206 of the enclosure 202. The integrated switch pad, shown in one exemplary embodiment in FIG. 2d, can include a plurality of switch zones 218. Each switch zone is configured to be actuated with a person's foot. In one embodiment, each of the switch zones can include a membrane switch. The membrane switch may be configured to provide a tactile response when the switch is actuated, such as a snap or spring type feeling. The tactile response can be implemented using a metal dome or a polymer dome formed using thermal processing that is located within the membrane switch. This tactile response provides feedback to a user to enable the user to sense when a switch on the integrated switch pad has been actuated. Alternatively, each membrane switch may have little or no tactile response to allow the switch to be actuated with minimal physical sense.

Figure 2E:
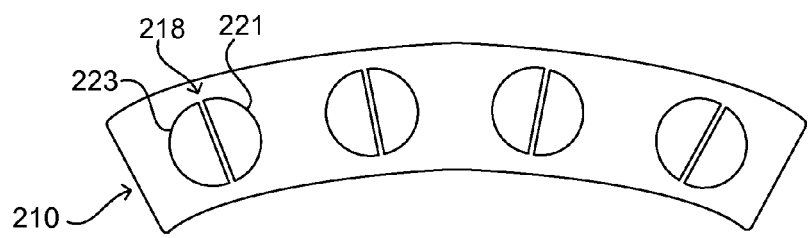
FIG. 2e is an illustration of an integrated switch pad containing a plurality of substantially flat switch zones with divided zones in accordance with an embodiment of the present invention.

In another embodiment, each switch zone 218 on the integrated switch pad 210 can be divided into a first switch 221 and a second switch 223, as illustrated in FIG. 2e. The first and second switches can be separated by a set distance, such as one fourth of an inch. In one embodiment, the switches can be connected in series to provide that both the first and the second switches are depressed in order to send a command from the wireless footswitch. Dividing the switch zone into at least two sections and requiring that each section is depressed to send a signal can substantially reduce the risk of a user accidentally depressing a switch, or placing their foot in a location on the switch pad that would unintentionally actuate two adjacent switches. In addition, the use of two switches connected in series can eliminate a potential single point of failure. For instance, if one switch in the switch zone were to malfunction, it would not result in the unintentional activation of the body scanning device. With the switch zones divided into two sections, a user would have to actuate four sections at one time in order to actuate two adjacent switch zones simultaneously. In one embodiment, each switch zone 218 can be separated by a distance of approximately fifteen inches. This broad separation, along with the division of the switch zones into multiple switches, can substantially eliminate the accidental actuation of two adjacent switches.

Figure 2F:
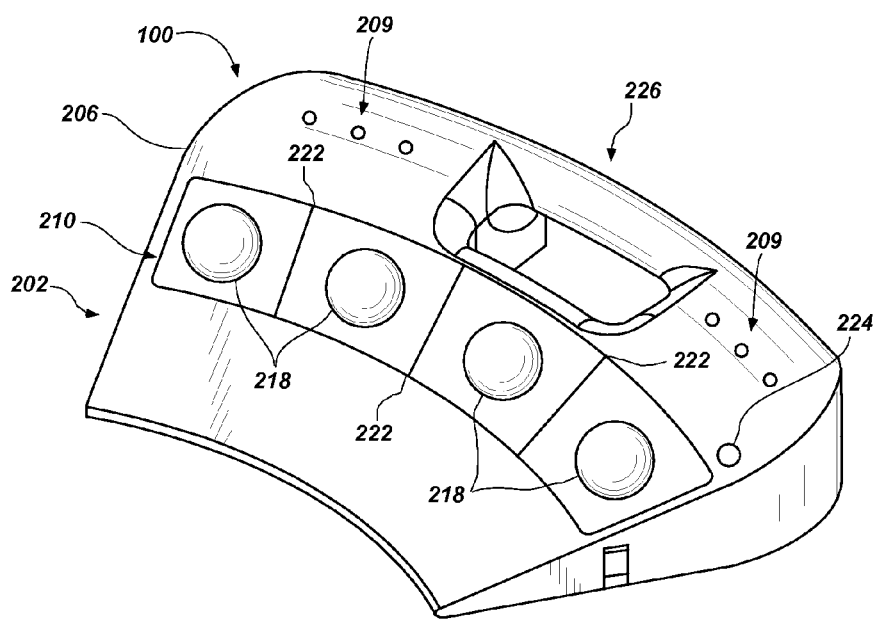
FIG. 2f is an illustration of the wireless footswitch in relation to the integrated switch pad in accordance with an embodiment of the present invention.

Additionally, an exemplary embodiment illustrated in FIG. 2f shows that the enclosure 202 can include at least one tactile feature 222 located between each switch zone 218 on the enclosure. The tactile feature allows the user to sense which of the switch zones is actuated on the footswitch system 100 without the need to look down to see where the user's foot is located on the enclosure. The tactile feature may be a ridge and/or groove integrated into the top surface 206 of the enclosure 202 between each switch zone 218. Alternatively, the tactile feature may be formed from a different material than the top surface is formed from, such as rubber or Velcro that allows the user to sense a transition between switch zones on the enclosure.

Figure 3:
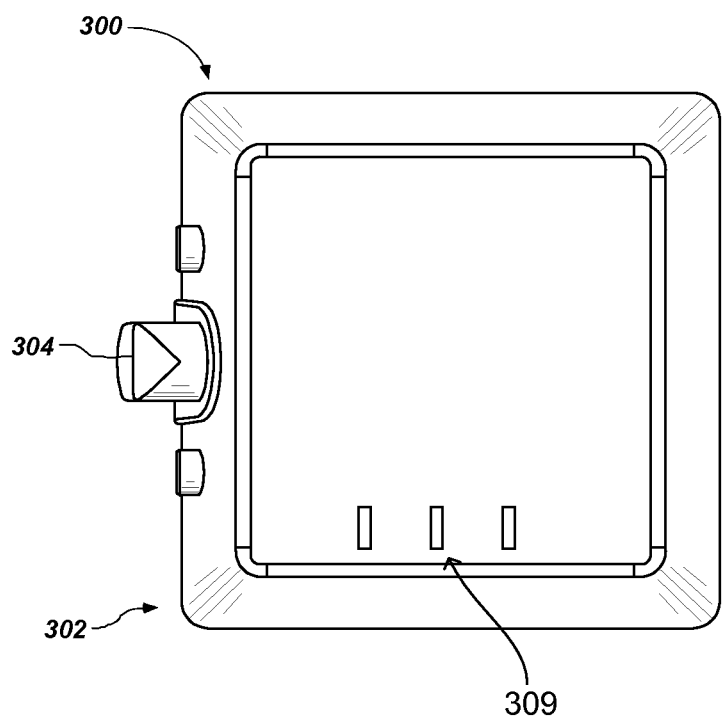
FIG. 3 is an illustration of a receiver operable to connect to a body-scanning device in accordance with an embodiment of the present invention.

The footswitch system 100 can also include sensors 209. The sensors can be optically coupled to light emitting devices such as light emitting diodes. The sensors typically are used in debugging to allow a user to verify proper operation and communication between the footswitch system 100 and the receiver 300 (FIG. 3). One or more sensors can be configured to output an optically encoded signal, such as a selected color or number of flashes to designate a specific operation or action at the secure transmitter.

In one embodiment, the enclosure 202 can include a handle 226. The handle area can improve the transportability of the footswitch system 100. The ability to easily transport the footswitch system enables it to be used at locations that are convenient rather than being limited by wiring or connection constraints. For example, a user can locate the footswitch system at a location where control of a scanning system is most comfortable and convenient to a patient. This can substantially improve the comfort and ease of a patient that is undergoing a scanning procedure. The handle also allows the footswitch system to be used with portable imaging devices that are frequently moved.

Certain types of body-scanning devices are typically operated in a darkened environment. The darkened environment may be used to allow the scanner operator to more easily view the scanned images. In this environment, it may be difficult for the user to see the switch zones 218 on the footswitch system 100. The switch zones formed of the membrane switch can be lighted to provide a visual feedback to allow the scanner operator to ensure that the proper switch is depressed while operating the body-scanner with the footswitch system. Lighting of the membrane switch zones can be accomplished using light emitting diodes, fiber optics, electroluminescence, and the like. Electroluminescent lighting can be provided by screen printing a printable ink deposit over a desired area of the membrane switch. The light can be substantially uniform over the desired area. The amount of light provided at each switch zone is typically small to reduce battery drain and minimize interference with the light emitted by scanning displays. A separate switch 224 may be included that enables an operator to activate or deactivate the switch zone lighting, as desired.

FIG. 3 illustrates one embodiment of the secure receiver 300. The secure receiver can be contained within a package 302 having a connector 304 designed to be connected to a scanning device, as previously discussed. The connector can be a multi-pin connector, a coaxial connector, or another type of connector typically used to input information into a body-scanning device. The receiver can also include sensors 309 used to verify operations and for debugging. The sensors can be optically coupled to light emitting devices such as light emitting diodes. One or more sensors can be configured to output an optically encoded signal, such as a selected color or number of flashes to designate a specific operation or action at the secure receiver.

Figure 4:
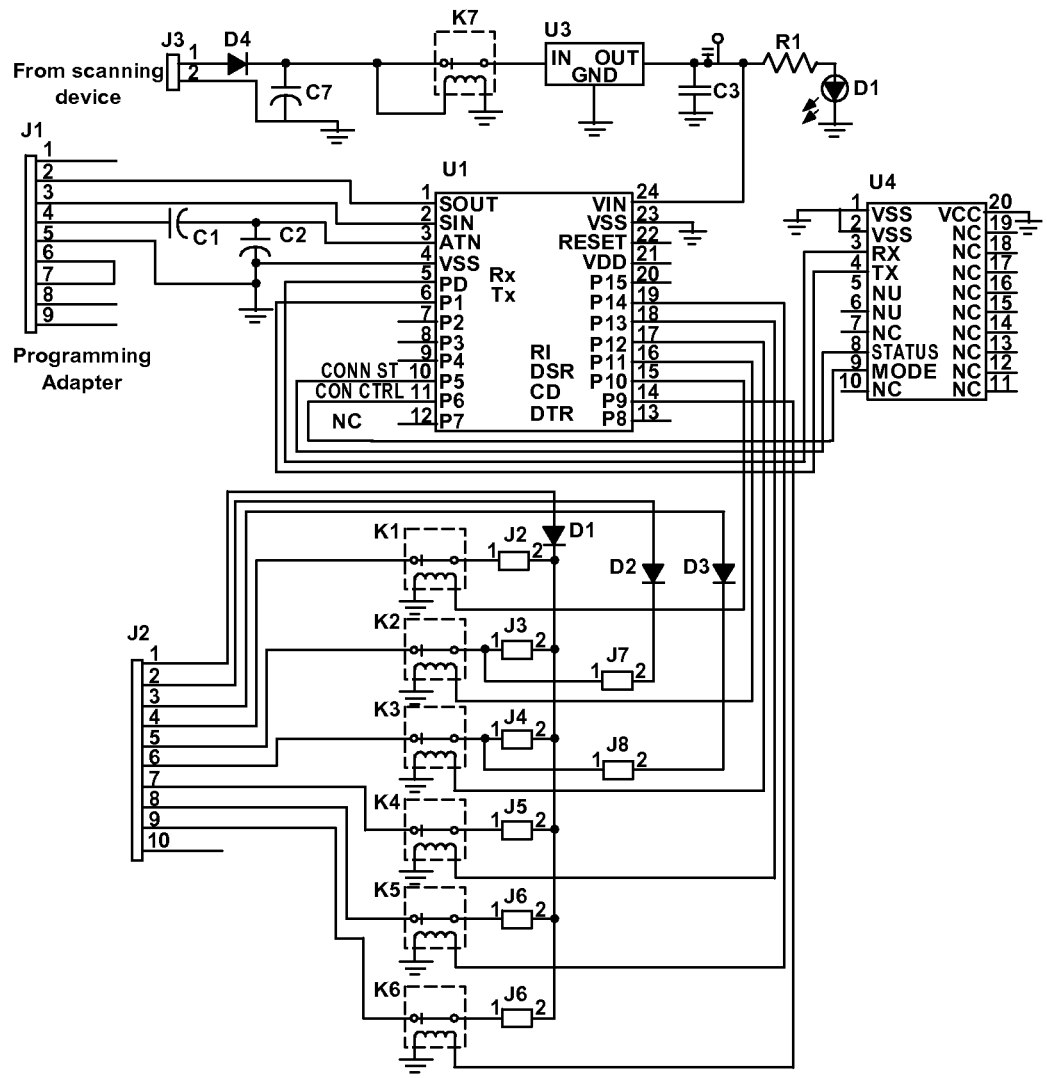
FIG. 4 is an illustration of an electrical schematic of the receiver in accordance with an embodiment of the present invention.

An exemplary embodiment of an electrical schematic for the receiver unit 300 is illustrated in FIG. 4. The receiver unit can be comprised of a microprocessor (U1), a transceiver (U4), and additional ancillary components. The microprocessor can be a basic stamp or another type of programmable microcontroller or microprocessor. For example, a BS2 Parallax basic stamp microcontroller may be used. The transceiver can be operable to communicate using the Bluetooth specification, the 802.11x specification, or another proprietary or publicly available communication scheme that can be used to provide secure wireless communications. For example, the transceiver can be an EB101 embedded Bluetooth radio. The microcontroller and microprocessor, while shown as discrete components, can be integrated in a printed circuit board design.

In the embodiment illustrated in FIG. 4, the microprocessor U1 can control the output relays (K1-K6) and the transceiver unit (U4). The microprocessor (U1) can interface with the relay set (K1-K6) using its I/O ports numbered P9-P14 (U1 pins 14-19). The microprocessor (U1) can also control the transceiver using its I/O pins 5, 6, 10 and 11 (P0, P1, P5, and P6). Power can be delivered to the various circuit components through connector J3. The power can typically be obtained from a power source in the body-scanning device. Incoming power is then routed through the steering diode (D4) and capacitor C7, to relay K7. The relay energizes when the power reaches 12 VDC. The power is then fed to voltage regulator U3, which reduces the input voltage to +5 VDC. The +5 VDC signal is then filtered and stored by capacitor C3 and directed to the input power pins of U1 and U3. Power is also passed across resistor R1 and onto LED D1, which illuminates and indicates that power is present on the printed circuit board. In one embodiment, pins P8 and P9 can be connected together with a logical AND to protect against a single mode failure of the microprocessor U1, caused by a shorted substrate. Additional light emitting diodes can also be included to provide indicators for debugging and connecting the wireless circuits.

Signals from the footswitch are received at the transceiver (U4). The transceiver then transmits them to the microprocessor (U1) in serial data format using U4 pins 3 and 4 and U1 pins 5 and 6 respectively, as shown. The microprocessor converts the serial data into a variable and selects the proper output port/relay over which to route the variable based on previous programming. The port or relay is activated by placing an active signal (+5 VDC) on the proper output port. The port is connected to and activates the correct relay(s). The information is then output through J2 to the body-scanning device. This can be accomplished using hardware, software, firmware, or some combination.

Figure 5A:
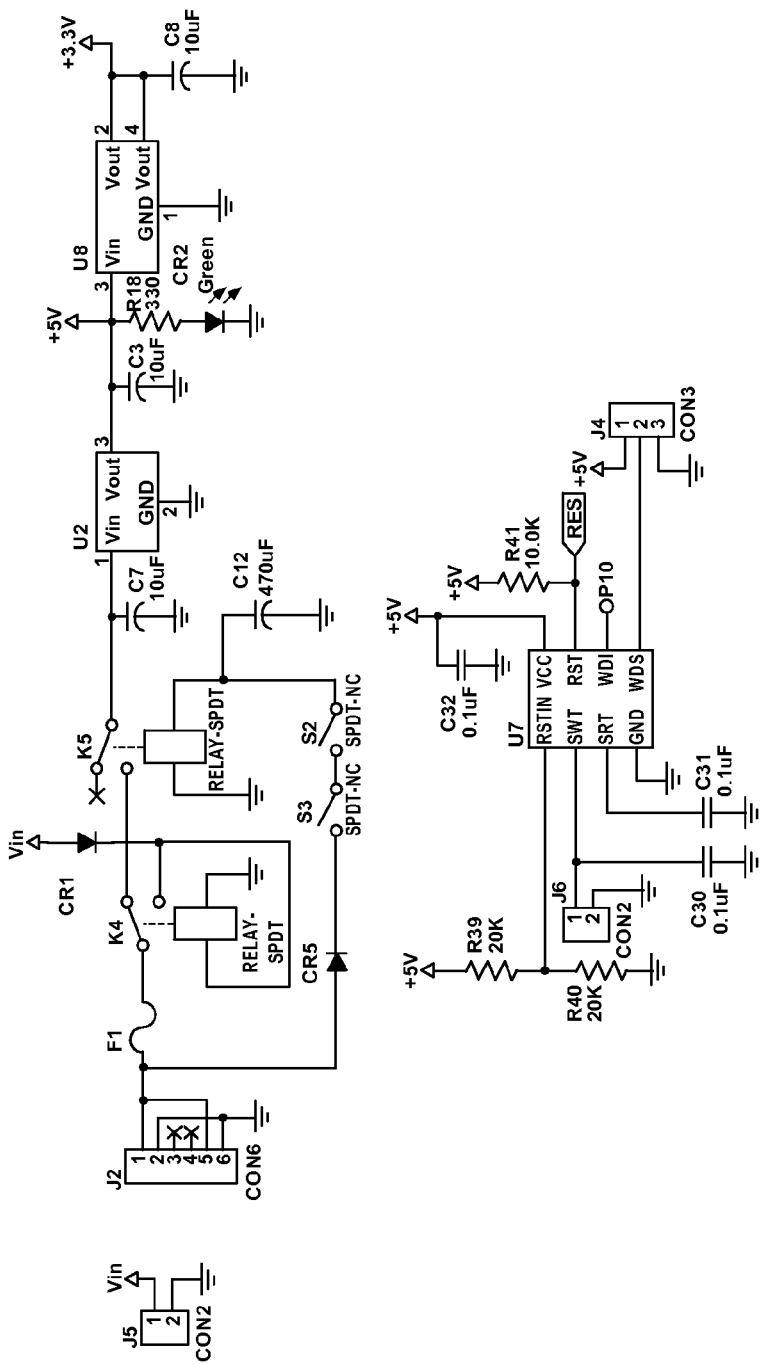
FIG. 5a is an illustration of an electrical schematic of a section of a transmitter for the wireless footswitch in accordance with an embodiment of the present invention.
Figure 5B:
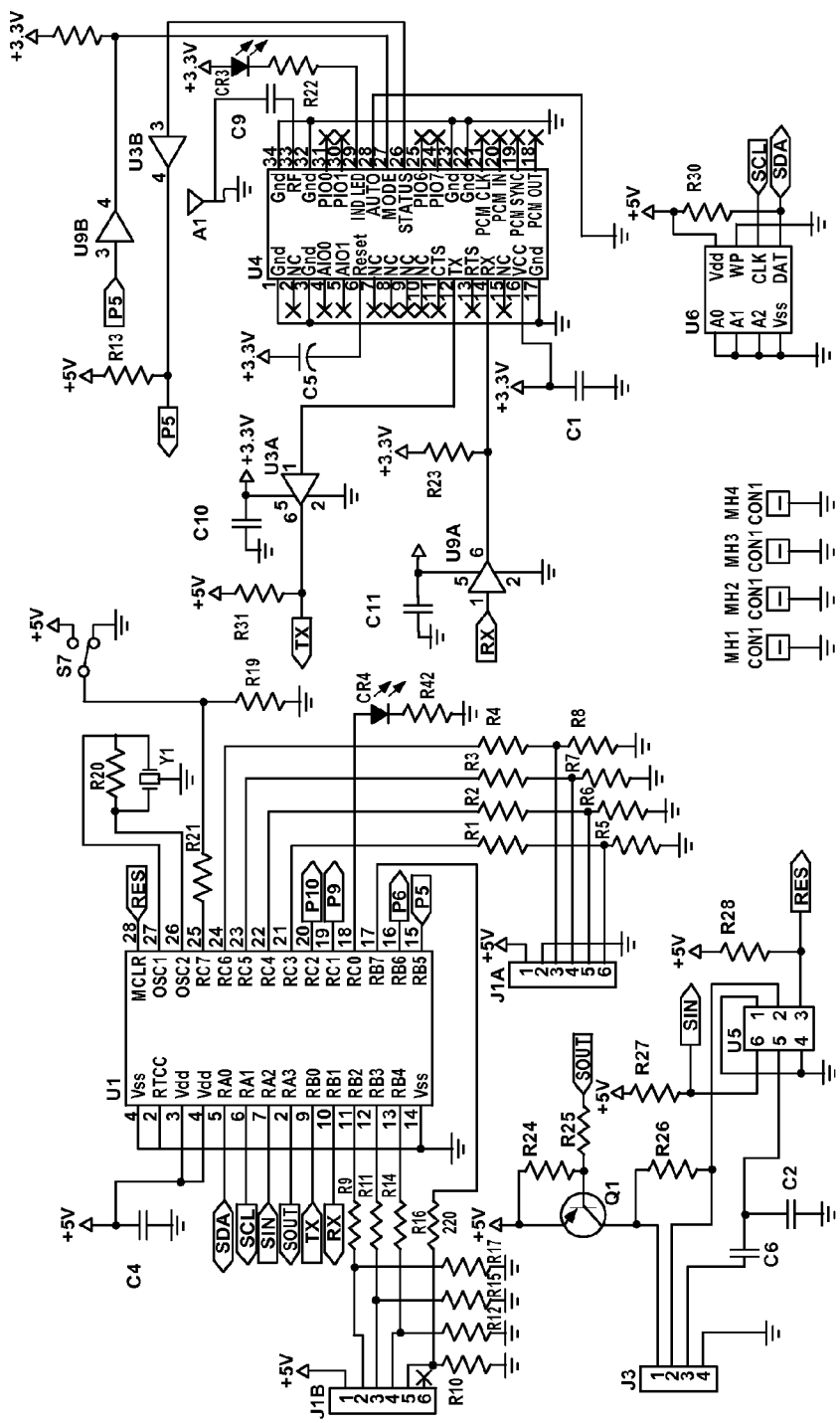
FIG. 5b is an illustration of an additional section of the electrical schematic of the transmitter for the wireless footswitch in accordance with an embodiment of the present invention.

An exemplary embodiment of an electrical schematic for a printed circuit board for the wireless transmitter in the footswitch 100 is illustrated in FIG. 5a and FIG. 5b. With reference to FIG. 5a, a charging input to the printed circuit board can be connected at J5. J5-pins 1 and 2 can be connected to a battery charger, such as a lithium ion charger circuit. Power from at least one rechargeable battery can be connected through J2. For example, in an embodiment with two batteries, the batteries positive leads can be connected to pins J2-1 and J2-5, and ground can be connected through pins J2-2 and J2-6. A fuse F1 is used to protect the connection between the batteries and the circuit.

In one embodiment, a gravity switch can be used to disable power to the transmitter when the footswitch is not on a flat surface. For example, when the transmitter circuit that is mounted in the wireless footswitch is changed from an upright position and placed substantially flat for use on a surface such as the floor, gravity switch S2 (or S3) actuates to turn on relay K5, thereby applying power to holding capacitor C7 and five volt regulator U2, which then outputs +5 VDC. The +5 VDC signal is then applied to the microprocessor U1. A capacitor C12 may be used to reduce the sensitivity of the gravity switch. Voltage regulator U8 is used to apply power to transceiver U4. This effectively powers the footswitch unit on. The microprocessor and transceiver can be the same as those used in FIG. 4. Ground is applied to the ground plane at the J5 connector and connects as shown on the schematic to provide current return to the power supply. Relay K5 will close when the gravity switch S2 closes. The gravity switch may also be connected as S3. When the charging voltage is removed, the relay K4 de-energizes and the batteries are reconnected to the working circuit as long as the gravity switch is closed.

The use of the gravity switch S2 provides an additional safety mechanism to help ensure the security of workers, patients, and the body-scanning device to which the footswitch is connected. When the footswitch is not laid substantially flat on a surface then power to the unit is turned off through gravity switch S2. This ensures that a button on the footswitch is not inadvertently activated while the wireless footswitch is being moved.

Additional safety measures can also be implemented in the footswitch transmitter. The use of radio transmitters and receivers is inherently more complicated than a wired connection. The increased complexity, comprising additional hardware, software, and firmware, can increase the potential for a temporary malfunction such as the inability to send a command from the footswitch that will be received and performed by the body-scanning device. The increased complexity and corresponding amplified potential for problems has historically limited the use of wireless communication to control of non-critical items.

The footswitch can be used to control body-scanning devices, which can output potentially dangerous forms of radiation and matter. In order to allow the convenience of wireless control while substantially reducing the potential risk of a hardware or software error to prevent a critical communication to the body-scanning device, additional safety components have been added to the footswitch controls. For example, FIG. 5a shows the use of a watchdog timer U7. An exemplary watchdog timer is a Maxim MAX6746KA29+T integrated circuit.

The watchdog timer can control the microprocessor reset line (U1, pin 28) from the U7 RST line. The microprocessor can toggle its P10 port high and then low at a regular interval during the course of its execution. The watchdog timer counts the toggles and maintains operation as long as the predetermined number of toggles occurs. If the hardware, such as processor U1, or the software running within the processor or other components connected to the processor cease to function normally (freeze up), thereby making the processor unable to execute its instructions, the watchdog routine will not toggle the WDI port on U7 and the watchdog timer will issue a reset to the microprocessor U1. The reset command will reset and restart the microprocessor and its associated code. This prevents the transmitter from encountering conditions in which a command cannot be sent, such as when the processor is stuck in a parasitic loop. The software toggling the watchdog can be used in a plurality of program locations where parasitic looping may occur. When the processor resets, the transmitter is configured to automatically turn off critical features such as X-ray emissions, proton beams, and the like. The use of the watchdog timer provides additional safety mechanisms that allow the wireless footswitch to be used to control critical hardware such as body-scanning devices while minimizing potential risks to operators and patients.

The footswitch microprocessor U1 can be a basic stamp or another type of programmable microcontroller or microprocessor. The microprocessor can be connected to the plurality of switches carried on the footswitch system. For example, in the exemplary embodiment shown in FIG. 5b, input ports RB2, 3, 4 and 7 are connected to switches on the footswitch system through connector J1B. The input ports are connected through a voltage divider network, which limits the input current and drops the voltage through the resistor to ground. The microprocessor can be a basic stamp, or another type of programmable microprocessor or microcontroller. In one embodiment, the microprocessor can be a BS2 Parallax basic stamp microcontroller. A predetermined routine can be used to poll and monitor the switches on the footswitch using the microprocessor, as can be appreciated.

Information from the microprocessor U1 can be communicated to a transceiver U4. In one embodiment, the transceiver can be the same as used in FIG. 4. The transceiver in the footswitch 100 can be configured to communicate with the transceiver in the receiver 300. The transceiver U4 can be operable to communicate using a Bluetooth specification, an 802.11x specification, or another proprietary or publicly available communication scheme that can be used to provide substantially secure wireless communications between the transceivers in the footswitch and the receiver.

In the exemplary embodiment shown in FIG. 5b, U1 pins 9 and 10 (P0 and P1) are connected to U4 pins 12 and 14 (transmit and receive) using a standard serial communications protocol that is built in to both U1 and U4, allowing for rapid communications and programming using a conventional graphical user interface.

Figure 7A:
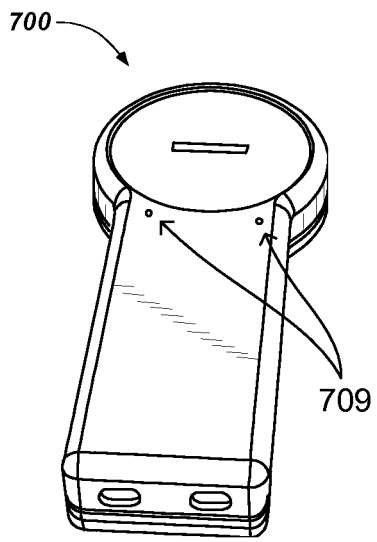
FIG. 7a is a perspective view illustration of a wireless handswitch in accordance with an embodiment of the present invention.
Figure 7B:
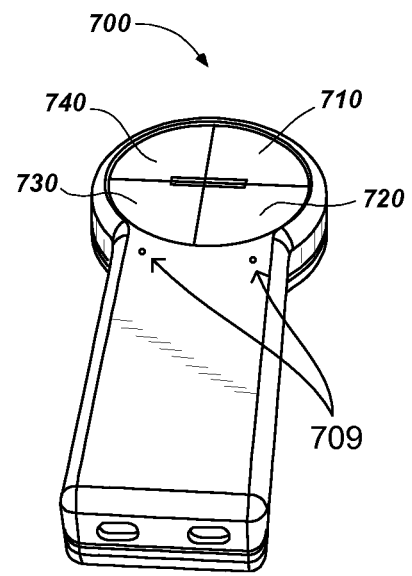
FIG. 7b is a perspective view illustration of the wireless handswitch of FIG. 7a showing a plurality of switch zones in accordance with an embodiment of the present invention.

In one embodiment, a handswitch can be used in conjunction with, or in place of the footswitch. In certain operating environments, it can be more convenient for a scanner operator to use a handswitch along with, or in lieu of the footswitch. An exemplary handswitch 700 is illustrated in FIG. 7a. The handswitch can include a plurality of switch zones, with each switch zone providing an independent switch that can be used to control functions of a body-scanning device. For example, FIG. 7b shows an exemplary illustration wherein the handswitch includes four separate switch zones, 710, 720, 730 and 740.

In one embodiment, the handswitch 700 can be in wireless communication with the footswitch. Indicators 709 can be used to debug the handswitch circuitry, to determine when the handswitch is in wireless communication with a receiver, or other indications as needed. The handswitch can operate substantially similarly to the operation of the footswitch that has been previously described. However, the handswitch can be configured to communicate with a receiver in the footswitch rather than directly with the receiver at the body-scanning device.

A wireless signal can be communicated from the handswitch 700 to the footswitch 100 (FIG. 2e). The wireless signal can include information detailing the status of each switch zone on the handswitch. The footswitch 100 can then transmit the information from the handswitch to the receiver 300 (FIG. 3). Using the footswitch as an intermediary to transmit the information to the receiver can enable a single, secure wireless channel to be created between the footswitch and the receiver. This eliminates the need for two separate receivers at the body-scanning device and reduces the overall complexity of the system, thereby reducing the cost of the footswitch/handswitch combination. Additionally, the handswitch can be designed to only communicate with the footswitch, thereby enabling secure communication from the handswitch to the footswitch and then to the receiver at the body scanning device. This provides secure communication from the handswitch to the receiver while substantially reducing potential interference with other wireless devices within a hospital or clinic. While examples are provided in which the handswitch can communicate via the footswitch, this is not intended to be limiting. The system can be configured to allow the footswitch to communicate via the handswitch to the receiver 300 (FIG. 3), as can be appreciated.

One exemplary illustration of a schematic for a handswitch transmitter configured to communicate with the footswitch is illustrated in FIGS. 6a(1)-6a(3). In the exemplary schematic for a handswitch transmitter, the remote handswitch can include a microprocessor U1 shown in FIG. 6a(1) that is operable to detect when a switch zone on the handswitch is depressed. In one embodiment, the microprocessor can be a BS2 Parallax basic stamp microcontroller. The microprocessor can communicate a change in status of one of the switch zones to the wireless transmitter U6, shown in FIG. 6a(3). In one embodiment, the wireless transmitter U6 can be an EB101 embedded Bluetooth radio. The wireless transmitter can be configured to transmit the status of the switch zones on the handswitch to a remote handswitch receiver located within the footswitch enclosure. In the exemplary embodiment illustrated in FIG. 5b, the remote handswitch receiver can be connected through connector J1A to inputs RC3, 4, 5 and 6 of U1. The signals are then interpreted by the microprocessor U1 and directed to the transceiver U6 to be transmitted to the receiver 300 (FIG. 3), as previously discussed.

An exemplary illustration of a schematic of a handswitch receiver 600 is provided in FIGS. 6b(1) and 6b(2). As discussed above, the handswitch receiver can be located in the footswitch enclosure 202 (FIG. 2a) and hardwired to the wireless footswitch transmitter, as shown in FIG. 5b. The handswitch receiver includes a transceiver U4 (FIG. 6b(2)) that can be configured to communicate with the transceiver U6 in the handswitch transmitter (FIG. 6a(3)). The transceiver U4 can be operable to communicate using a Bluetooth specification, an 802.11x specification, or another proprietary or publicly available communication scheme that can be used to provide substantially secure wireless communications between the transceivers in the footswitch and the receiver. In one embodiment, the transceiver U4 can be an EB101 embedded Bluetooth radio.

Data from the handswitch transmitter transceiver U6 (FIG. 6a(3)) can be received at U4 in FIG. 6b(2) and communicated to a microprocessor U1 shown in FIG. 6b(1). In one embodiment, the microprocessor U1 can be a BS2 Parallax basic stamp microcontroller. In the exemplary embodiment shown in FIG. 6a(1), U1 pins 9 and 10 (RB0 and RB1) are connected to U4 pins 12 and 14 (transmit and receive) using a standard serial communications protocol that is built in to both U1 and U4. The microprocessor can be used to process the received signals and convert the data to a desired format. The formatted data can then be output from pins 18 to 21 to connector J3. Connector J3 can be connected to connector J1A of FIG. 5b, as previously discussed.

In one embodiment, the transceivers U4 in FIGS. 5b and 6b can be configured such that communication from either the handswitch or the footswitch is given priority. For example, in the exemplary embodiment of FIGS. 5b and 6b, pin RB6 of U1 is connected to pin 27 of U4. The microprocessor can be used to change the mode of the transceiver based on whether the footswitch, the handswitch, or some combination will be used. It is also possible for the handswitch to communicate directly with the receiver 300 (FIG. 3).

The data from the microprocessor U1 in FIG. 6a(1) may be scrambled using encryption algorithms, error correction encoding and so forth. The transceiver U6 shown in FIG. 6a(3) can wirelessly transmit symbols corresponding to the scrambled data from the microprocessor U1. The scrambling of the data can ensure that only a desired device can receive and interpret the data, thereby substantially reducing unintended operation of extraneous medical devices. Additionally, the symbols that are transmitted can also be spread using a pseudorandom noise (PN) code. Spreading of the symbols can minimize the probability that the data can be detected and received by a non-intended receiver that does not have knowledge of the specific PN code. The data may also be transmitted using multiplexing such as time or space division multiplexing.

The symbols transmitted from the transceiver U6 in the handswitch transmitter illustrated in FIG. 6a(3) can be received by the transceiver U4 in the handswitch receiver illustrated in FIG. 6b(2). The secure receiver can detect, receive, despread, decrypt, and demultiplex the symbols as necessary to convert the symbols to data. The secure receiver may include error correction decoders to minimize transmission and reception errors in the symbols communicated between the secure transmitter and secure receiver. This information can then be communicated to the microprocessor U1 shown in FIG. 6b(1). The microprocessor can also be used in despreading, decrypting, and demultiplexing the symbols as necessary.

In one embodiment, each handswitch zone can include at least two switches connected in series to eliminate a potential single point of failure of a switch in the handswitch zone, as previously discussed with respect to the switches connected in series in the footswitch zone.

The transmitters and receivers in the handswitch and footswitch are typically shown in the previously described examples as being integrated within the respective enclosures. However, this is not intended to be limiting. For example, wireless transceivers may also be externally connected to the handswitch and footswitch. For instance, an IEEE 802.11 transceiver dongle or a Bluetooth transceiver dongle may be attached to one of the handswitch and footswitch via a standard connection such as a USB connection, or the like. The transceiver can then communicate with a processor in the enclosures, as previously described to communicate with the receiver 300 to enable an operator of a body-scanning device the ease and convenience of wirelessly controlling the scanning device from a desired location using one or both of the handswitch enclosure and the footswitch enclosure.

Figure 8:
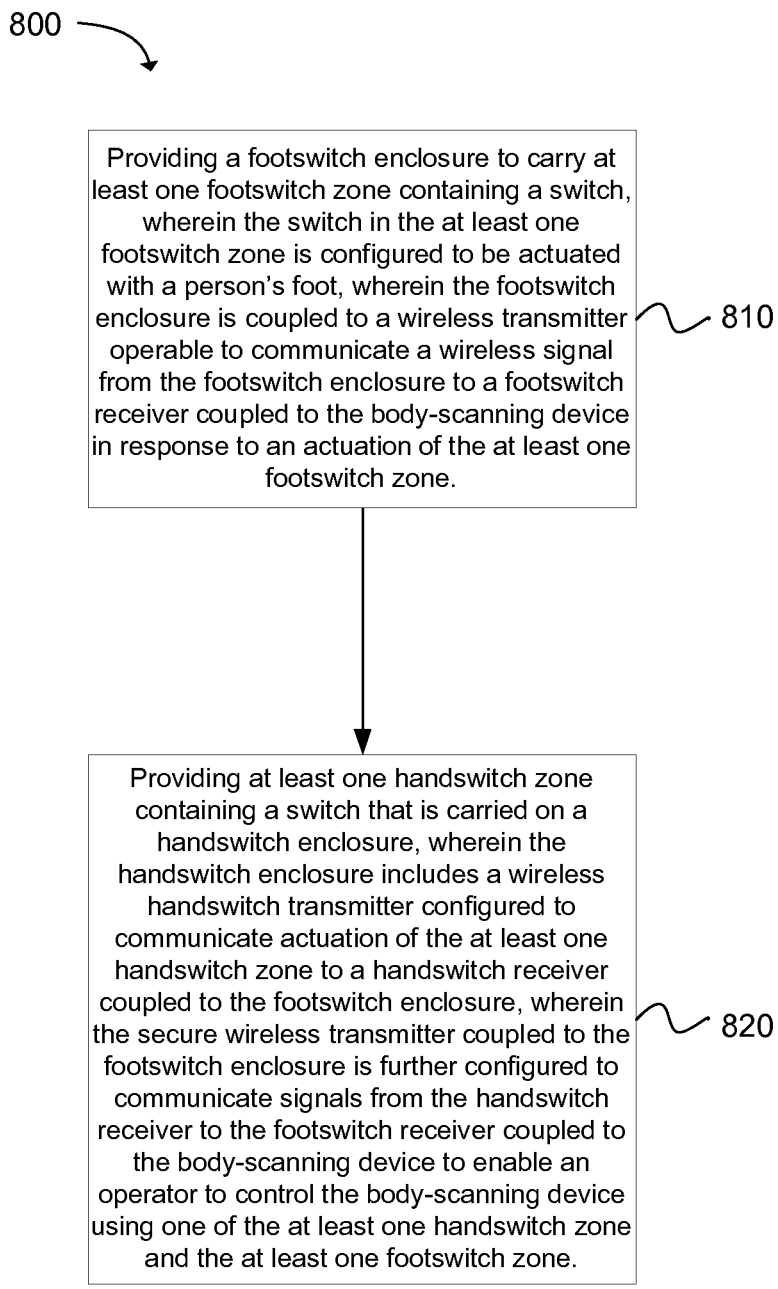
FIG. 8 is a flow chart depicting a method for wirelessly controlling a body-scanning device in accordance with an embodiment of the present invention.

In another embodiment, a method 800 for wirelessly controlling a body-scanning device using multiple wireless devices is depicted in the flow chart of FIG. 8. The method includes the operation of providing 810 a footswitch enclosure. The footswitch enclosure can carry at least one footswitch zone. Each footswitch zone includes a switch that is configured to be actuated with a person's foot. The footswitch enclosure can be coupled to or integrated with a wireless transmitter operable to communicate a wireless signal from the footswitch enclosure to a footswitch receiver coupled to the body-scanning device. The wireless signal can be communicated in response to an actuation of the at least one footswitch zone.

An additional operation includes providing 820 at least one handswitch zone containing a switch that is carried on a handswitch enclosure. The handswitch enclosure includes a wireless handswitch transmitter configured to communicate actuation of the at least one handswitch zone to a handswitch receiver located in the footswitch enclosure. The secure wireless transmitter that is coupled to or located within the footswitch enclosure is further configured to communicate signals from the handswitch receiver to the footswitch receiver coupled to the body-scanning device to enable an operator to control the body-scanning device using one of the at least one handswitch zone and the at least one footswitch zone.

The wireless footswitch system 100 and wireless handswitch 700 are operable to communicate securely with the receiver 300 to enable an operator of a body-scanning device the ease and convenience of wirelessly controlling the scanning device from a desired location. The desired location can be selected to provide more convenience and comfort to a patient. The hardware and software are designed to provide a high degree of reliability needed to control critical medical instruments that are designed to emit potentially harmful radiation.

Additionally, the wireless footswitch is designed to provide an operator of a body-scanning device with an ergonomic design. The ergonomic design of the wireless footswitch does not require the operator to lift his or her entire foot to actuate an adjacent switch zone. This reduces strain and fatigue that can occur during long scanning procedures.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

What is claimed is:

1. A wireless control system for communicating with a body-scanning device using multiple wireless devices, comprising:
    a footswitch enclosure;
    at least one footswitch zone containing a switch carried on the footswitch enclosure, wherein the switch in the at least one footswitch zone is configured to be actuated with a person's foot;
    a wireless transmitter coupled to the footswitch enclosure and configured to form a wireless connection between the wireless footswitch and a footswitch receiver coupled to the body-scanning device to communicate actuation of the footswitch zone to enable an operator to control the body-scanning device using the footswitch;
    a handswitch enclosure;
    at least one handswitch zone carried on the handswitch enclosure containing a switch, wherein the switch in the at least one handswitch zone is configured to be actuated with a person's hand; and
    a wireless handswitch transmitter coupled to the handswitch enclosure and configured to communicate actuation of the at least one handswitch zone carried on the handswitch enclosure to a handswitch receiver coupled to the footswitch enclosure, wherein the wireless transmitter coupled to the footswitch enclosure is further configured to communicate signals from the handswitch receiver to the footswitch receiver coupled to the body-scanning device to enable an operator to control the body-scanning device using at least one of the handswitch zone and the footswitch zone.

2. A system as in claim 1, further comprising a microprocessor electrically connected to the wireless transmitter coupled to the footswitch enclosure, wherein the microprocessor is operable to scan a status of the switch in each of the at least one footswitch zones and the at least one handswitch zone.

3. A system as in claim 2, further comprising a watchdog timer configured to receive a pulsed signal from the microprocessor that is pulsed at a predetermined rate when the microprocessor is operating within selected parameters, wherein the watchdog timer is operable to reset the microprocessor when the pulsed signal is pulsed at less than the selected rate.

4. The system of claim 3, wherein the wireless transmitter is a secure wireless transmitter that is operable to transmit a signal to the body-scanning device to turn off an output of the body scanning device when the pulsed signal is pulsed at less than the selected rate.

5. A system as in claim 2, further comprising a priority switch coupled to the microprocessor, wherein the priority switch is operable to select between the communication of actuation of the at least one footswitch zone and communication of actuation of the at least one handswitch zone to the footswitch receiver coupled to the body-scanning device.

6. The system of claim 1, wherein the body-scanning device is selected from the group consisting of a fixed x-ray emitting device, a portable x-ray emitting device, a fluoroscope, a magnetic resonance imager, a nuclear magnetic imager, an ultrasound imager, and a proton scanner.

7. The system of claim 1, wherein the at least one footswitch zone contains at least two switches connected in series, with the at least two switches in the footswitch zone configured to be actuated to actuate the footswitch zone.

8. The system of claim 1, wherein the at least one handswitch zone contains at least two switches connected in series, with the at least two switches in the handswitch zone configured to be actuated to actuate the handswitch zone.

9. The system of claim 1, wherein the wireless footswitch receiver is configured to recognize only the wireless transmitter coupled to the footswitch enclosure during a paring operation.

10. The system of claim 9, wherein the wireless footswitch receiver and the wireless transmitter coupled to the footswitch enclosure are placed in non-discoverable mode after pairing to provide enhanced security.

11. The system of claim 1, wherein at least one of the footswitch zones on the footswitch enclosure and the handswitch zones on the handswitch enclosure are illuminated to enable the wireless control device to be used in a darkened environment.

12. The system of claim 1, wherein the wireless transmitter coupled to the footswitch enclosure is operable to transmit scrambled data and the footswitch receiver coupled to the body-scanning device is operable to receive the scrambled data and descramble the data and communicate the descrambled data to the body scanning device.

13. The system of claim 1, wherein the handswitch transmitter is operable to transmit scrambled data and the handswitch receiver is operable to receive the scrambled data and descramble the data and communicate the descrambled data to the secure wireless transmitter for communication to the secure wireless receiver and the body scanning device.

14. A method for wirelessly controlling a body-scanning device using multiple wireless devices, comprising:
    providing a footswitch enclosure to carry at least one footswitch zone containing a switch, wherein the switch in the at least one footswitch zone is configured to be actuated with a person's foot, wherein the footswitch enclosure is coupled to a wireless transmitter operable to communicate a wireless signal from the footswitch enclosure to a footswitch receiver coupled to the body-scanning device in response to an actuation of the at least one footswitch zone; and
    providing at least one handswitch zone containing a switch that is carried on a handswitch enclosure, wherein the handswitch enclosure includes a wireless handswitch transmitter configured to communicate actuation of the at least one handswitch zone to a handswitch receiver coupled to the footswitch enclosure, wherein the secure wireless transmitter coupled to the footswitch enclosure is further configured to communicate signals from the handswitch receiver to the footswitch receiver coupled to the body-scanning device to enable an operator to control the body-scanning device using one of the at least one handswitch zone and the at least one footswitch zone.

15. A method as in claim 14, further comprising selecting between a priority of communication of actuation of the at least one footswitch zone and communication of actuation of the at least one handswitch zone to the footswitch receiver coupled to the body-scanning device.

16. A method as in claim 14, further comprising:
providing that the footswitch zone and the handswitch zone each include at least two switches connected in series; and
identifying that one of the footswitch zone and the handswitch zone have been actuated when each of the at least two switches located in the respective footswitch zone and the handswitch zone have been actuated.

17. A method as in claim 16, further comprising monitoring a condition of the microprocessor to determine when the microprocessor is operating within predetermined parameters and transmitting a signal to the footswitch receiver coupled to the body-scanning device to turn off an output of the body-scanning device when the microprocessor is operating outside of the predetermined parameters.

18. A method as in claim 17, further comprising monitoring the condition of the microprocessor using a watchdog timer configured to receive a pulsed signal from the microprocessor that is pulsed at a predetermined rate when the microprocessor is operating within the predetermined parameters, wherein the watchdog timer is operable to reset the microprocessor when the pulsed signal is pulsed at less than the predetermined rate.

19. A method as in claim 14, further comprising illuminating at least one of the at least one footswitch zone and the at least one handswitch zone to enable the wireless control of the body-scanning device in a darkened room.

20. A method as in claim 14, further comprising providing an integrated switch pad carried on a footswitch enclosure containing a plurality of substantially flat footswitch zones with a tactile divider located between each footswitch zone to provide feedback to a user concerning a location of the user's foot on the footswitch enclosure.

\* \* \* \* \*